United States Patent [19]

Kreitmair et al.

[11] Patent Number: 4,873,446
[45] Date of Patent: Oct. 10, 1989

[54] DEVICE FOR IRRADIATING DENTURE PARTS

[76] Inventors: Albert Kreitmair, Forstenrieder Allee 233b, 8000 München 71; Günther Nath, Delpstrasse 27, 8000 München 80, both of Fed. Rep. of Germany

[21] Appl. No.: 218,472

[22] Filed: Jul. 6, 1988

Related U.S. Application Data

[63] Continuation of Ser. No. 9,613, Jan. 22, 1987, which is a continuation of Ser. No. 487,577, Apr. 22, 1983.

[30] Foreign Application Priority Data

Apr. 27, 1982 [DE] Fed. Rep. of Germany ....... 3215664
Aug. 4, 1982 [DE] Fed. Rep. of Germany ....... 3229117
Sep. 15, 1982 [DE] Fed. Rep. of Germany ....... 8226016
Oct. 4, 1982 [DE] Fed. Rep. of Germany ....... 8227782

[51] Int. Cl.⁴ ............................................. C08J 7/18
[52] U.S. Cl. ............................. 250/492.1; 250/504 R; 250/455.1
[58] Field of Search ............. 250/492.1, 504 R, 455.1

[56] References Cited

U.S. PATENT DOCUMENTS

| 3,627,590 | 12/1971 | Mammel | 148/1.5 |
| 3,693,623 | 9/1972 | Harte et al. | 128/303.1 |
| 3,822,706 | 7/1974 | Simone et al. | 128/396 |
| 3,956,201 | 5/1976 | Seiner | 260/2.5 M |
| 4,167,669 | 9/1979 | Panico | 250/504 |
| 4,421,987 | 12/1983 | Herold | 250/492.1 |
| 4,433,244 | 2/1984 | Hogan | 250/455.1 |
| 4,571,665 | 2/1986 | Herold et al. | 250/492.1 |

FOREIGN PATENT DOCUMENTS

| 2607249 | 8/1977 | Fed. Rep. of Germany . |
| 1411677 | 10/1975 | United Kingdom . |
| 1450009 | 9/1976 | United Kingdom . |
| 1581998 | 12/1980 | United Kingdom . |
| 2098439 | 11/1982 | United Kingdom . |

OTHER PUBLICATIONS

Jenkins et al., *Fundamentals of Optics*, 3rd Edition, 1957, pp. 284–285.

*Primary Examiner*—Jack I. Berman
*Attorney, Agent, or Firm*—Handal & Morofsky

[57] ABSTRACT

An irradiation device for the radiation polymerization of synthetic materials in denture parts is described, having an electric lamp as source for radiation in the shortwave visible and close ultraviolet spectral region, also having a receptacle defining an irradiation chamber for a denture part which is to be irradiated, and a concave reflector associated with the lamp to reflect the radiation of the lamp into the irradiation chamber, and the said irradiation device contains a xenon flashlight as an electric lamp which has a curved bulb which extend in two directions of a surface. The bulb of the flashlight preferably has the shape of a helix with approximately 1½ windings and tangentially spaced straight ends. The reflector is preferably box-shaped and has an open narrow side through which the connection ends of the flashlight bulb extend. The receptacle is preferably a dish with a quadrangular cross-section made from PTFE which surrounds the denture part with a clearance.

13 Claims, 5 Drawing Sheets

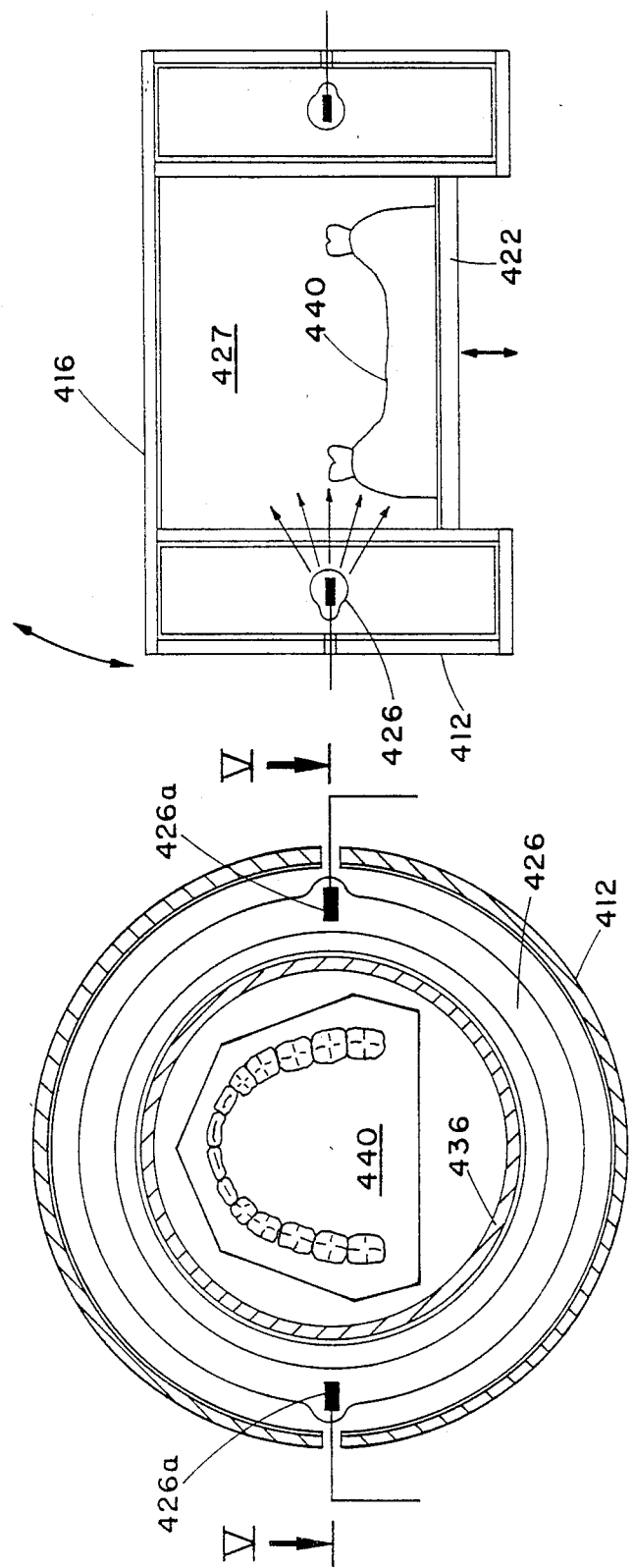

DEVICE FOR IRRADIATING DENTURE PARTS

This application is a continuation of application Ser. No. 009,613 filed Jan. 22, 1987, which is a continuation of application Ser. No. 487,577 filed Apr. 22, 1983.

The present invention relates to an irradiation device for the radiation polymerisation of synthetic materials in denture parts.

Irradiation devices are known from U.S. Pat. No. 3,627,590 which contain two opposing concave reflectors. An electric lamp which serves as the radiation source is arranged in one reflector, whilst the other serves to receive the part to be irradiated and contains retaining means therefor.

German Offenlegungsschrift No. 2607249 discloses an irradiation device for the ultraviolet spectral region which contains a tungsten-halogen lamp as a radiation source, a photoconductor and a dielectric thin layer filter which reflects the shortwave proportion of the radiation from the lamp in the photoconductor and allows the undesired long-wave proportion of the radiation to pass through.

Nowadays denture parts are generally produced with synthetic materials which can be polymerised by radiation in the shortwave proportion of the visible spectral region and by radiation in close ultraviolet light. For such denture parts an irradiation device which permits intensive, uniform all-round irradiation of the synthetic parts is required for polymerisation. The object of the present invention is to provide such an irradiation device which ensures uniform, intensive all-round irradiation of denture parts, is robust, economical and reliable in operation and can be easily maintained if necessary.

Above all short polymerisation times should be achieved for large denture parts, such as multi-section bridges and full prostheses.

An irradiation device according to the invention, which is designed specially for the short-wave part of the visible spectral region and optionally close ultraviolet light, contains as an essential component a flashlight which at least partially encloses (e.g. U-shaped or circular) an irradiation chamber or a flashlight which is elongated viewed from the irradiation chamber, especially a xenon lamp with a tubular curved bulb which extend in two dimensions of a surface and therefore occupies a specific surface and is preferably at least 80 mm long.

The bulb of the flashlight preferably has the shape of a helix which has one complete winding and parallel ends which are remote therefrom in the same direction, so that the wound part of the bulb extends over approximately 540 degrees. However, the bulb of the flashlight can also be circular, U-shaped, W-shaped, S-shaped or Z-shaped.

In a preferred embodiment of the invention a box-type reflector, especially one which is substantially in the shape of a truncated pyramid, which is made from dielectric material is associated with the flashlight. The reflector preferably consists of flat thin layer interference filter plates which are cemented together. The thin layer interference filter is preferably designed so that it reflects radiation in the range from approximately 300 to 520 Nonometres but allows longer-wave radiation to pass through. However, the reflector can also be made completely or at least on its surface from microcrystalline pblytetrafluoroethylene (PTFE).

The receptacle for the denture part to be irradiated defines the irradiation chamber and is preferably a thick-walled dish made from PTFE or ceramic. The thickness of the wall will generally be between approximately 2 and 5 mm, especially approximately 4 mm. The dish preferably has an approximately square cross-section with rounded corners and preferably has holes, e.g. in the base, to facilitate the passage of cooling air.

A thick-walled dish made from PTFE has the essential advantage that the synthetic material to be polymerised, e.g. a facing of the denture part, remains relatively cold and therefore contracts less during polymerisation because of the permeability of PTFE for long-wave radiation. Despite the relatively high transparency of PTFE this advantage is achieved without significantly lengthening the polymerisation time by comparison with a metal reflector since the short-wave radiation is scattered back through the microcrystalline PTFE into the irradiation chamber. It has also been shown that the irradiation of the synthetic material to be polymerised is very uniform. The PTFE retains these advantageous properties, whilst metal reflectors rapidly become matt and clouded. The dish encloses the denture part with considerable clearance and therefore does not touch the synthetic material to be polymerised or only touches it on regions of small surface area, so that uniform irradiation is ensured. The noise generated by the flashlight working in pulse operation can be kept to a low level by a series of measures which can be applied alone, but preferably in combination with several or all such measures. The xenon pressure in the flashlight should be in the range between 20 kPa and and 55 kPa (approximately 150 and 400 Torr) and can preferably be 36.5 kPa (approximately 275 Torr).

The bulb of the flashlight preferably has a length between approximately 150 and 400 mm, most advantageously approximately 250 mm, and an internal diameter between 4 and 10 mm, preferably approximately 7 mm.

The pulse length should be between 0.1 and 2 ms and preferably 0.4 ... 0.5 ms.

The pulse repetition frequency should be between 10 and 60 Hertz and should preferably be an integral fraction of the mains frequency, particularly half the mains frequency (25 or 30 Hz).

The operating voltage of the lamp can be between 600 and 2000 Volts, depending upon the bulb diameter, bulb length and filling pressure. The average electric power consumption of the flashlight at the most preferred values referred to above can be approximately 350 W.

It is also advantageous for the flashbulb to be fired in such a way that firing occurs shortly after the peak of the mains voltage half wave which charges the storage capacitor, that is to say during the branch of the charging voltage which is falling to zero.

These advantageous features are preferably applicable to all embodiments of the invention.

In the drawings:

FIG. 4 shows a horizontally cut plan view of a part of an irradiation device according to a second embodiment of the invention;

FIG. 5 shows a vertical section in a plane V—V in FIG. 4; and

Figure 1:
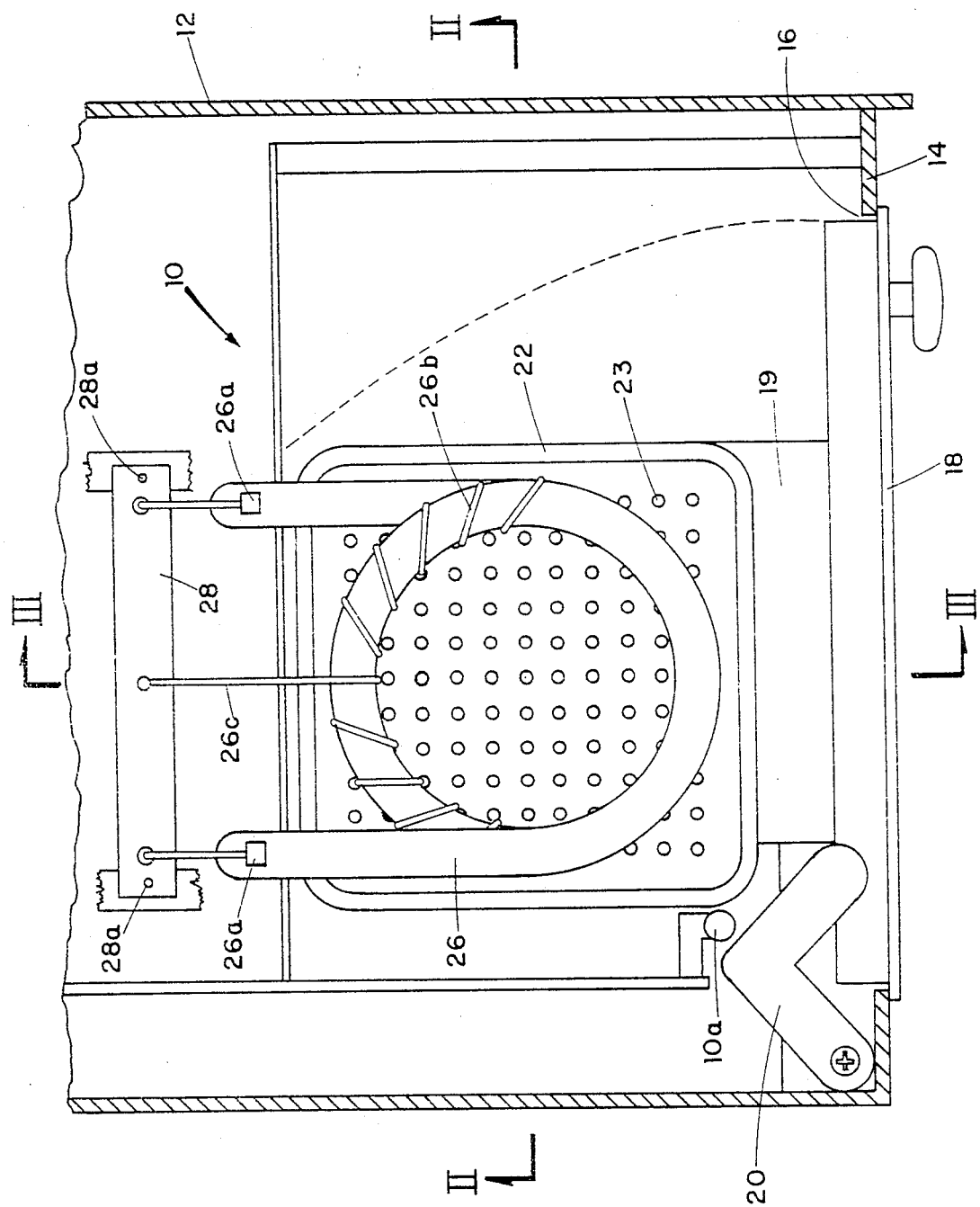
FIG. 1 shows a horizontally cut plan view of a part of an irradiation device according to one embodiment of the invention.
Figure 2:
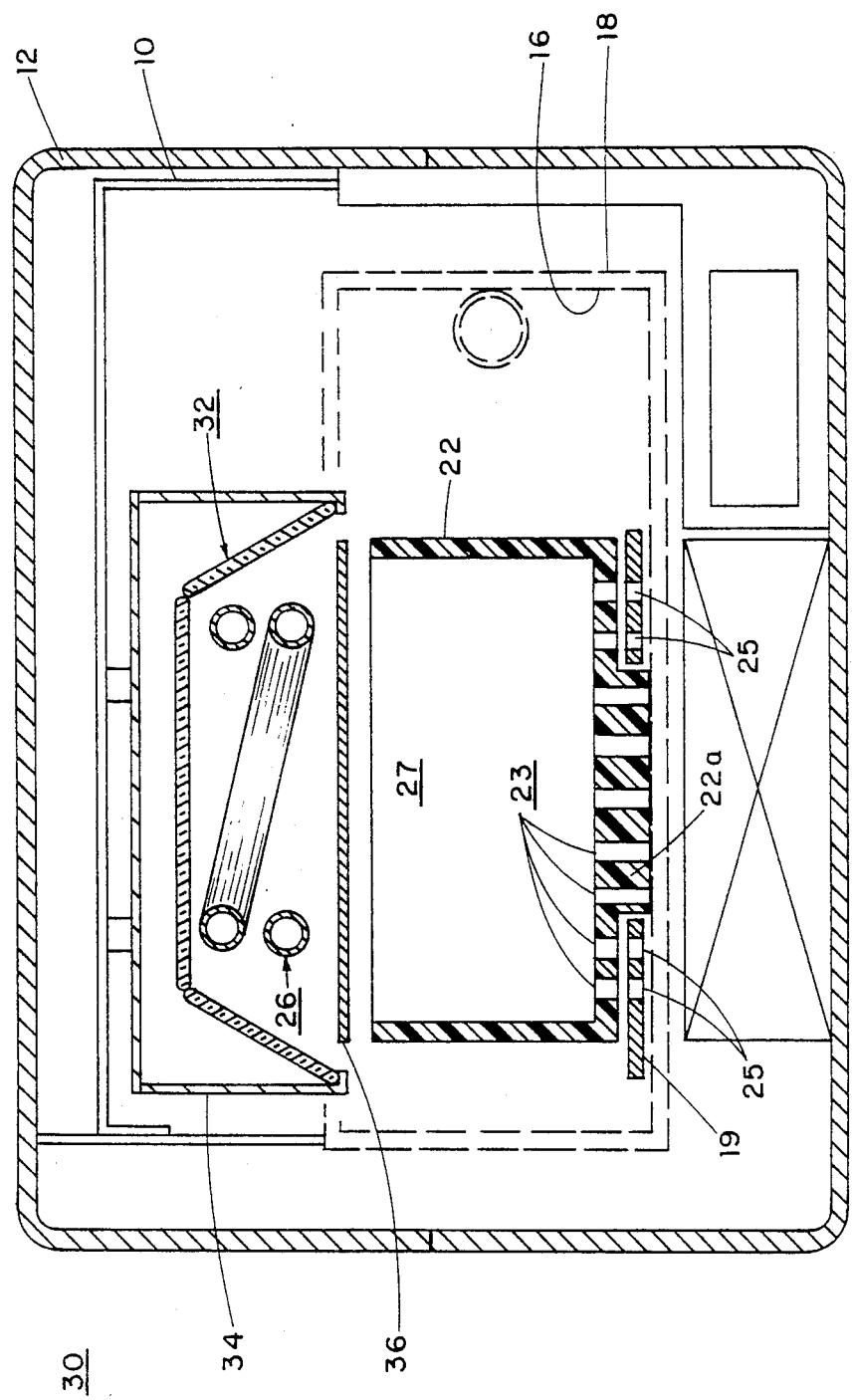
FIG. 2 shows a vertical section in a plane II—II in FIG. 1.
Figure 3:
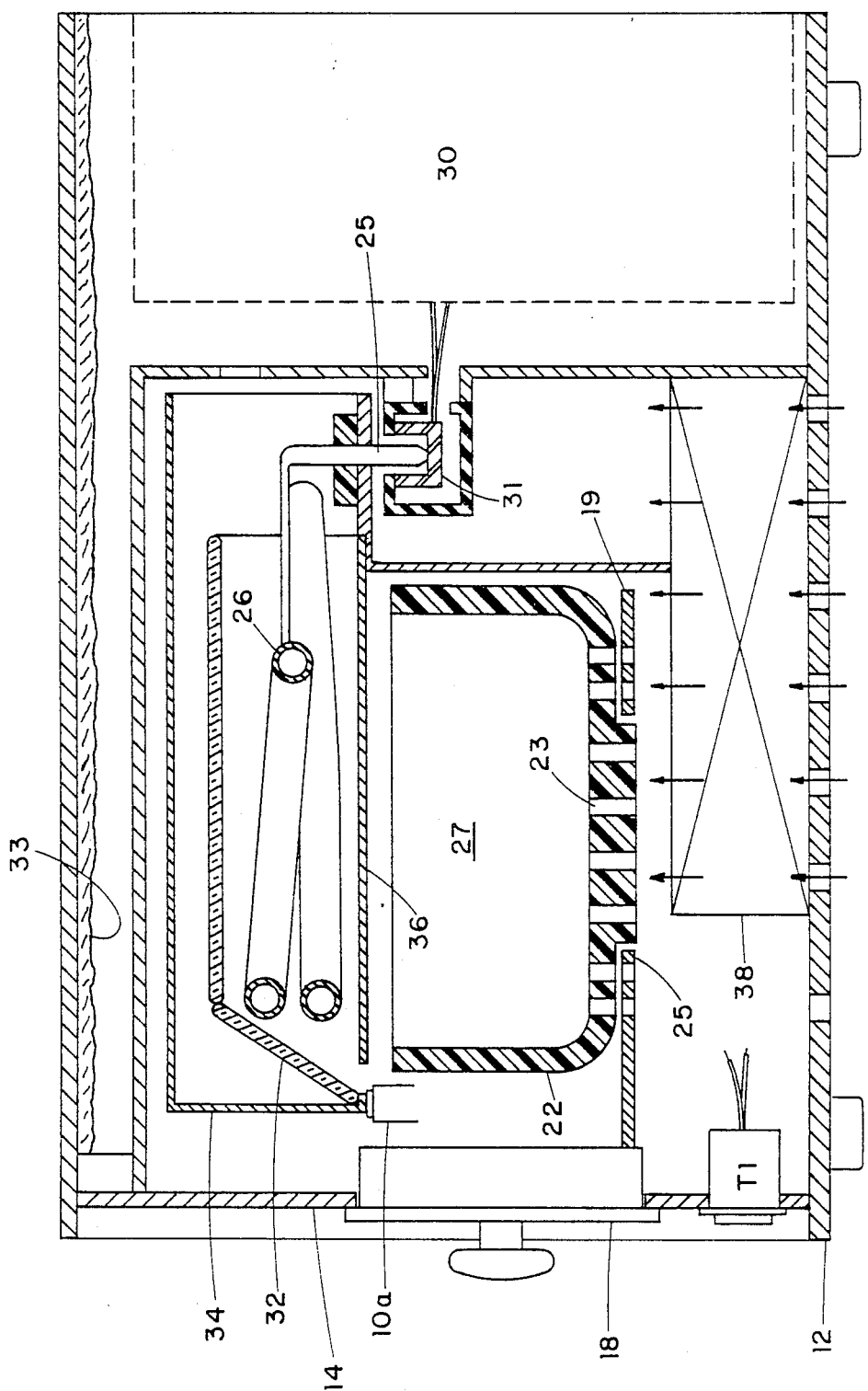
FIG. 3 shows a section in a plane III—III in FIG. 1.

The embodiment of the irradiation device according to the invention which is preferred at present is illustrated in FIGS. 1 to 3. This irradiation device contains a frame 10 which is arranged in an outer housing 12. The frame 10 has a front plate 14 with an opening 16 which can be closed by a door 18. The door is fastened on the front plate 14 by a hinge 20. A horizontal retaining plate 19 for a receptacle for a denture parts, not shown, which is to be treated is mounted on the inside of the door 18. In the illustrated preferred embodiment of the invention the receptacle consists of a thick-walled dish 22 which is approximately square in cross-section and is made from white microcrystalline PTFE. The thickness of the walls of the dish is approximately 3 to 4 mm. The corners of the dish are rounded (FIG. 1). At the bottom of the base of the dish is a rectangular projection 22a which fits into a corresponding recess in the retaining plate 19 so that the dish 22 sits securely in the retaining plate 19 but can be easily removed. The base of the dish 22 is provided with holes 23 for cooling air. Where the underside of the dish 22 rests on the retaining plate 19 the latter is provided with corresponding holes 25 which align with the holes 23.

The interior of the dish 22 forms an irradiation chamber 27. A xenon flashlight 26 is arranged above the irradiation chamber 27. The flashlight 26 has a tubular helical bulb which forms one complete winding and one half winding and has parallel ends in which cylindrical tungsten self-baking electrodes 26a are located. The flashlight also has a firing electrode 26b in the form of a thin wire which surrounds the bulb helically and has a connection 26c. The length of the discharge space in the bulb between the electrodes 26a is approximately 250 mm. The external diameter of the helix is approximately 55 mm. The internal diameter of the bulb is approximately 7 mm and the filling pressure is approximately 34.6 to 37.2 kPa (260 to 280 Torr). The lamp is operated with a current of approximately 1500 Volts. Since this xenon flashlight has a relatively long discharge space and a relatively high filling pressure, a large amount of effective short-wave (blue) radiation is produced. The said parameters also mean that the short pulse-like discharges with which the flashlight is operated are accompanied by a relatively low noise. The baked tungsten electrodes 26a ensure a long life.

The connections of the lamp are connected to a plug strip 28 which is mounted by means of two screws 28a on an inwardly curved edge of a removable lamp housing 34. The plug strip 28 has three attaching plugs 29 which can be inserted into a socket 31 which is mounted on the frame 10 and is connected to an electronic circuit 30 which serves to supply the flashlight and will be discussed in greater detail with reference to FIG. 6. At the other end the lamp housing rests on at least one support 10a mounted on the frame 10.

As FIGS. 2 and 3 show, the flashlight 26 is arranged in a concave reflector 32 which is box-shaped, in particular approximately in the shape of a truncated pyramid, and is composed of flat dielectric thin layer interference reflectors and is open on the connection side of the lamp (on the right in FIG. 3). The reflectors contain a dielectric layer structure which reflects the useful short-wave radiation in the wavelength range from approximately 300 to 520 mm into the treatment chamber 27, whilst undesirable longer-wave thermal radiation is allowed to pass through and is absorbed by the lamp housing 34 which surrounds and retains the reflector 32. A flat thin layer interference filter 36 which permits the shorter-wave useful radiation to pass through into the interior of the treatment chamber 27 but reflects the undesirable longer-wave radiation is arranged on the lower open end of the reflector.

A schematically represented axial blower 38 which draws in cooling air through openings in the base of the outer housing 12 and conveys it upwards through the openings in the retaining plate 19 and in the base of the dish 22 is arranged in the lower part of the housing. The lamp housing 34 is also provided with openings (not shown) on its narrow lateral surfaces and on its upper surface for cooling air to pass through.

For damping noise the outer housing 12 can be provided on the inside with a sound-absorbing layer 33.

In FIGS. 4 and 5 the treatment chamber and the light source arrangement of another embodiment of the irradiation device are shown. This irradiation device contains an annular xenon flashlight 426 with tungsten self-baking electrodes 426a, also a cylindrical housing 412 and a cylindrical heat shield filter 436 which corresponds to the filter 36 in FIG. 1. The housing preferably, consists of a glass tube which is provided on the inside with a mirror coating, preferably a thin layer mirror analogous to the reflector 32 in FIG. 1. These parts coaxially enclose a cylindrical treatment chamber in which a denture part 440 which is to be polymerised is arranged. The denture part to be irradiated rests on a disc-like base 422 which can be adjusted in height and which can consist for example of a relatively thick PTFE or ceramic plate.

The annular xenon flashlight 426 can have an average radius of 50 to 60 mm and contain xenon at a filling pressure of for example 17.5 kPa (approximately 130 Torr). The treatment chamber 427 can be accessible through a hinged cover 416.

The housing 412 and the cover 416 can also be made from metal or synthetic material, e.g. PTFE, with a mirror coating on the inside, and in the latter case can have a thickness of approximately 2 to 5 mm, particularly approximately 3 mm.

The cover 416 can also be made from a transparent material, such as glass, and can be provided with a mirror coating so that it is possible to observe the treatment chamber without shielding or harming the eyes.

Figure 6:
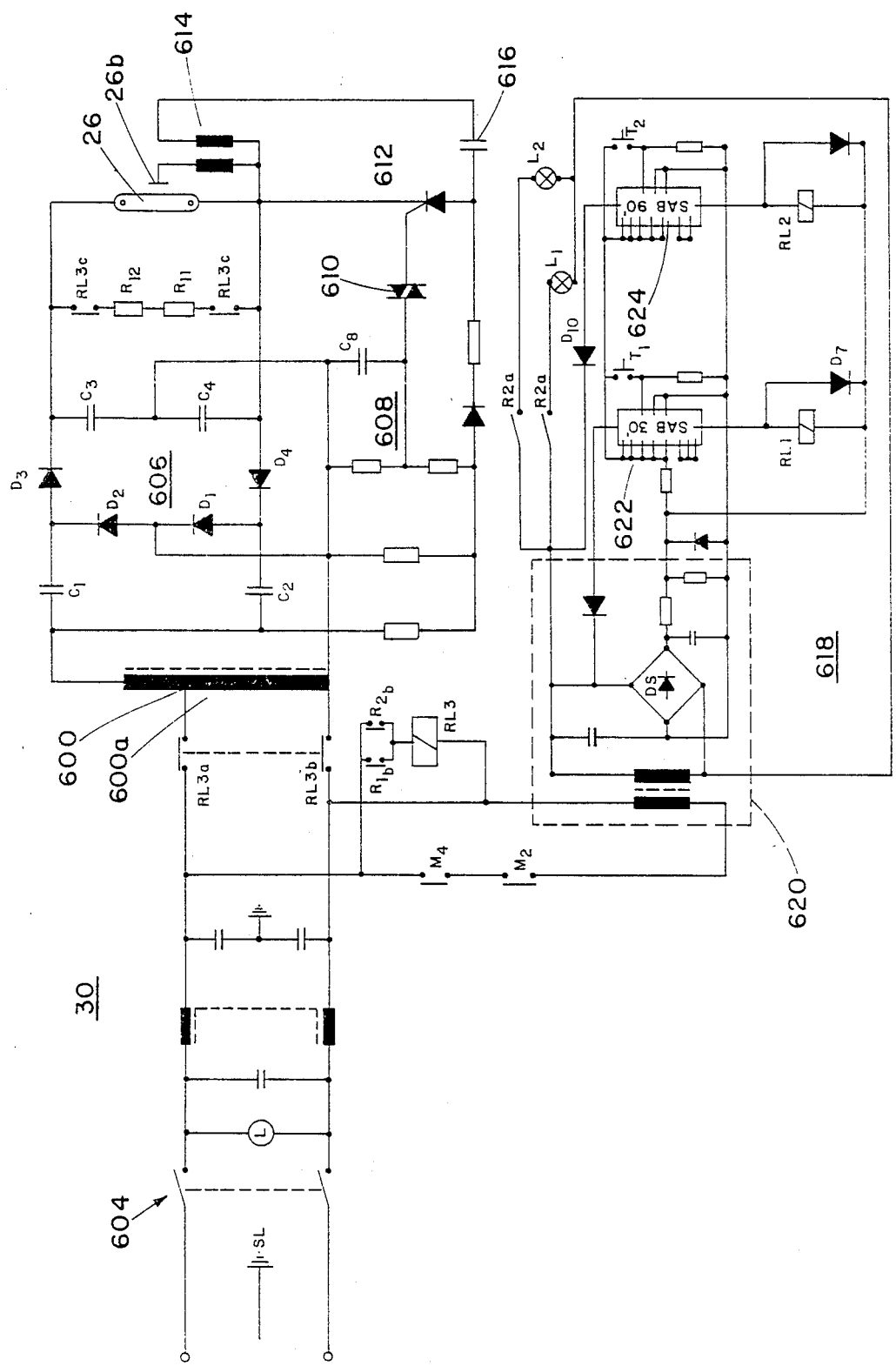
FIG. 6 shows a circuit diagram for the irradiation device according to FIGS. 1 to 3 or according to FIGS. 4 and 5.

The preferred electric circuit arrangement shown in FIG. 6 for supplying the flashlight 26 contains an autotransformer 600 the primary winding part 600a of which is connected to the alternating mains current by means of relay contacts RL3a and RL3b, an interference elimination filter 602 and a master switch 604. The transformer 600 supplies a highly transformed current of for example 360 Volts to a voltage quadrupler circuit 606 on the output terminals of which an average voltage of approximately 1500 V occurs and the discharge space of the flashlight 26 is connected. The voltage quadrupler circuit contains capacitors C1 to C4 and diodes D1 to D4 which are connected in the manner illustrated. A unipolar voltage consisting of half wave pulses of the mains voltage is tapped from the connection of the capacitors C1 and C2 and is supplied to a firing circuit 608 which contains a time constant circuit with a capacitor C8, a diac 610 and a firing thyristor 612 to which the primary winding of a firing transformer 614 is connected via a capacitor 616. The diac 610 responds at every second half wave pulse so that the thyristor 612 fires with half the mains frequency. The secondary winding of the starter transformer 614 then supplies a firing voltage pulse of approximately 20 kV to the firing electrode 26b of the flashlight.

The irradiation time is controlled by a timer circuit 618 which contains a power supply 620 and two integrated circuits 622 and 624 which serve as timers for two different irradiation times, e.g. 30 seconds and 90 seconds, and are controllable by means of switches T1 and T2 respectively arranged on the front plate 14. The timers control a relay RL1 or RL2. The relays close, on response, relay contacts R1a or R2a by means of which indicator lights L1 or L2 arranged in the keys of the switches are switched on, and contacts R1b or R2b, closure of which excites a relay RL3 which then closes the operating contacts RL3a and RL3b which are arranged in the mains supply lines to the tranformer 600. The relay RL3 also has rest contacts RL3c which open when the relay responds and are connected in series with discharge resistors R11, R12 between the output terminals of the circuit 606 so that the capacitors of the circuit 606 are automatically discharged when the mains current is switched off from the transformer 600.

Protective circuit breakers Ml and M2 are also provided which open when the doors 14 are opened or the outer housing 12 is removed and make the power supply 620 dead. The relays RL1, RL2 and thus also the relay RL3 cannot then be switched or drop so that the transformer 600 cannot be switched on or off and the output of the circuit 606 is bridged by the discharge resistors Rll, R12.

The embodiments described above can be varied in the most different ways and should not be regarded as limiting.

We claim:

1. Irradiation device for treating a synthetic material in denture parts, said device comprising an electric lamp for emitting useful radiation in a short-wave visible and near ultraviolet spectral ranges and undesired IR radiation; a receptacle defining a cup shaped irradiation chamber for a denture part to be irradiated; said chamber having a radiation entrance opening facing said lamp; and a concave reflector associated with said lamp to reflect the useful radiation from th elamp toward the radiation entrance opening of said irradiation chamber and to allow passage of the undesired radiation out of said irradiation device, wherein said concave reflector has essentially the shape of a truncated pyramid for reflecting the useful radiation of said lamp, and wherein said electric lamp is a xenon flashlamp, which has a curved bulb extending in two dimensions in a plan view of said radiation entrance opening of said irradiation chamber, said two dimensions being normal to a vertical axis of said irradiation chamber, said concave reflector being comprised of flat thin-film dielectric interference filter panes, said irradiation chamber being defined by walls, at least at the inner surface thereof, made of a material selected from the group comprising PTFE and ceramic and including a support surface for accomodating denture parts of various sizes, and a flat pane thin-film interference filter provided between said lamp and said irradiation chamber, said filter provided between said lamp and said irradiation chamber transmitting useful radiation of shorter wavelength while reflecting said undesirable IR radiation of longer wavelength.

2. Irradiation device as claimed in claim 1, wherein said interference filter panes reflect radiation in the wavelength range from approximately 300 to 520 Nanometers and transmit radiation of longer wavelength.

3. Irradiation device as claimed in claim 1, wherein said receptacle defining the irradiation chamber is made from microcrystalline PTFE with a wall thickness of at least 2 mm.

4. Irradiation device as claimed in claim 1, wherein said receptacle is retained so as to be removable in retaining means which are in turn mounted on a hinged door on a housing.

5. Irradiation device as claimed in claim 1, wherein said receptacle has holes for cooling air.

6. Irradiation device as claimed in claim 1, wherein the receptacle has rounded corners.

7. Irradiation device as claimed in claim 1, wherein:
 (a) the bulb of the flashlamp has the shape of a helix with approximately $1\frac{1}{2}$ winding and tangentially spaced parallel straight ends, comprising electrical connection means,
 (b) the reflector is box-shaped and has an open narrow side through which the connection ends of the flashlamp bulb extend; and
 (c) the receptacle is a dish with a rectangular cross-section and made from PTFE.

8. Irradiation device as claimed in claim 1, wherein said flashlamp has a tubular bulb which has electrodes at its end and has a length measured between the electrodes of approximately 200 to 300 mm and an internal between 5 and 9 mm, said bulb containing xenon at a pressure between approximately 250 and 300 Torr and the electrode comprises sintered tungsten bodies.

9. Irradiation device as claimed in claim 1, wherein the flashlamp is retained in a lamp housing by a plug strip which has attaching plugs for lamp electrodes of the flashlamp; the reflector is mounted in a lamp housing; and the arrangement consisting of the lamp housing, reflector flashlamp and plug strip is connected by the plugs of the plug strip to retaining means in the device so as to be easily removable.

10. Irradiation device as claimed in claim 1, further comprising an electronic circuit to supply the flashlamp with a succession of short voltage pulses, the average electric power consumption being approximately 200 to 450 Watts.

11. Irradiation device as claimed in claim 10, wherein the shape of the bulb of said flashlamp is selected from the group comprising helical shape, circular shape, U-shape, S-shape, Z-shape, W-shape.

12. Irradiation device as claimed in claim 1, wherein the reflector associated with the lamp is a solid PTFE member having a wall with a thickness of at least 1 mm.

13. Irradiation device as claimed in claim 1, wherein the shape of bulb of said flashlamp is selected from the group comprising helical shape, circular shape, U-shape, S-shape, Z-shape, W-shape.

* * * * *